(12) United States Patent
Mijolovic et al.

(10) Patent No.: US 7,288,614 B2
(45) Date of Patent: Oct. 30, 2007

(54) SUBSTITUTED CYCLOALKANES, AND USE THEREOF AS CATIONIC POLYMERIZATION INITIATORS

(75) Inventors: Darijo Mijolovic, Mannheim (DE); Mirjam Herrlich-Loos, Mannheim (DE); Gabriele Lang, Mannheim (DE); Herbert Mayr, Starnberg (DE)

(73) Assignees: BASF Aktiengesellschaft, Ludwigshafen (DE); Ludwig-Maximilians-Universitaet, Munich (DE)

( * ) Notice: Subject to any disclaimer, the term of this patent is extended or adjusted under 35 U.S.C. 154(b) by 0 days.

(21) Appl. No.: 10/578,185

(22) PCT Filed: Nov. 4, 2004

(86) PCT No.: PCT/EP2004/012498

§ 371 (c)(1),
(2), (4) Date: May 4, 2006

(87) PCT Pub. No.: WO2005/044766

PCT Pub. Date: May 19, 2005

(65) Prior Publication Data

US 2007/0123677 A1 May 31, 2007

(30) Foreign Application Priority Data

Nov. 5, 2003 (DE) ................. 103 51 643

(51) Int. Cl.
*C08F 4/14* (2006.01)
*C08F 10/10* (2006.01)
*C07C 23/16* (2006.01)

(52) U.S. Cl. ...................... 526/209; 526/135; 526/213; 526/237; 526/348.7; 570/186; 570/190; 568/670; 560/193

(58) Field of Classification Search ................ 526/135, 526/209, 213, 237, 348.7; 570/186, 190; 568/670; 560/193
See application file for complete search history.

(56) References Cited

U.S. PATENT DOCUMENTS 4,942,210 A * 7/1990 Kuntz ...................... 526/348.7
7,001,966 B2 * 2/2006 Lang et al. .............. 526/348.7

FOREIGN PATENT DOCUMENTS

EP 0 713 883 5/1996
WO 02/096964 12/2002

* cited by examiner

*Primary Examiner*—Fred Teskin
(74) *Attorney, Agent, or Firm*—Oblon, Spivak, McClelland, Maier & Neustadt, P.C.

(57) ABSTRACT

Substituted 7- to 12-membered cycloalkanes which have leaving groups, in particular chlorine atoms, on tertiary ring carbons, a process for preparing them and their use as initiators for cationic polymerization, in particular the cationic polymerization of isobutene are described. Preferred compounds are 1,4-dichloro-1,4-dimethylcyclooctane, 1,5-dichloro-1,5-dimethylcyclooctane and mixtures thereof. They are prepared by addition of hydrogen chloride onto appropriately substituted cycloalkapolyenes.

11 Claims, No Drawings

SUBSTITUTED CYCLOALKANES, AND USE THEREOF AS CATIONIC POLYMERIZATION INITIATORS

Substituted cycloalkanes, and use thereof as cationic polymerization initiators

The present invention relates to substituted cycloalkanes which have leaving groups on tertiary ring carbons, a process for preparing them and their use as initiators for cationic polymerization, in particular the cationic polymerization of isobutene.

The preparation of isobutene polymers by cationic polymerization (also referred to as "living cationic polymerization") is carried out using initiator systems which comprise a Lewis acid and an organic compound which reacts with the Lewis acid to form a carbocation or a cationogenic complex.

Isobutene polymers which are particularly useful for further processing, for example to produce sealant compositions or to produce adhesives or raw materials for adhesives, are ones which are telechelic, i.e. they have two or more reactive end groups. These end groups are especially carbon-carbon double bonds which can be functionalized further or groups which have been functionalized by a terminating agent. Thus, EP-A 713 883 describes the preparation of telechelic isobutene polymers using an at least bifunctional initiator such as dicumyl chloride. A disadvantage of the known method is that the aromatic initiators described can react to form indanyl or diindane groups (cf. Cr. Pratrap, S. A. Mustafa, J. P. Heller, J. Polym. Sci. Part A, Polym. Chem. 1993, 31, pp. 2387-2391), which has an adverse effect on the synthesis of defined telechelic isobutene polymers.

There continues to be a need for new initiators for cationic polymerization.

It is an object of the present invention to provide new initiators for cationic polymerization, in particular the cationic polymerization of isobutene. The initiators should not have the abovementioned disadvantages, and be easy to prepare and storage-stable.

We have found that this object is achieved by a substituted cycloalkane comprising a 7- to 12-membered carbocyclic ring of the formula I

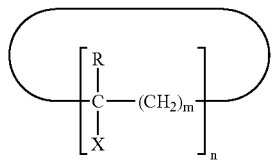
(I)

where
R is $C_1$-$C_6$-alkyl,
X is halogen, $OR^1$ or $OCOR^1$, where $R^1$ is $C_1$-$C_6$-alkyl,
n is 2 or 3 and
m is an integer of at least 1, preferably at least 2.

X, R and m can have different meanings in each repeating unit. Preference is given to X and R having the same meaning in each repeating unit.

The expression $C_1$-$C_6$-alkyl refers to linear or branched alkyl groups having from 1 to 6 carbon atoms, e.g. methyl, ethyl, n-propyl, isopropyl, n-butyl, sec-butyl, isobutyl, ter-tbutyl, n-pentyl, 2-methylbutyl, neopentyl, n-hexyl, 2-methylpentyl, 3-methylpentyl, 2,2-dimethylbutyl, 2,3-dimethylbutyl or 2-ethylbutyl.

Halogen is preferably chlorine, bromine or iodine, particularly preferably chlorine or bromine and especially chlorine.

R is preferably $C_1$-$C_4$-alkyl, more preferably methyl or ethyl, in particular methyl.

X is preferably halogen, acetyloxy or propionyloxy; methoxy, ethoxy, propoxy or butoxy, particularly preferably halogen and in particular chlorine.

The cycloalkanes of the formula I are 7- to 12-membered carbocyclic rings, preferably 7-, 8- or 9-membered carbocyclic rings. Particular preference is given to 8-membered rings.

The tertiary carbon atoms bearing the groups X are separated by at least one methylene group, preferably at least 2 methylene groups.

Preferred cycloalkanes of the formula I are those of the formulae Ia to Ic below, where
o=1 and p=2, or
o=1 or 2, p=2 or 3 and o+p=4, or
o=1 or 2, p=3 or 4 and o+p=5:

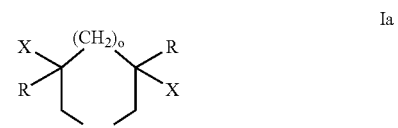
Ia

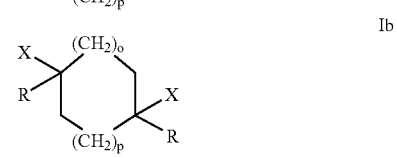
Ib

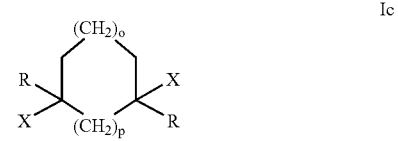
Ic

Particularly preferred substituted cycloalkanes of the formula I are 1,5-dichloro-1,5-dimethylcyclooctane and 1,4-dichloro-1,4-dimethylcyclooctane of the formulae Id and Ie, respectively, where R is methyl and X is Cl.

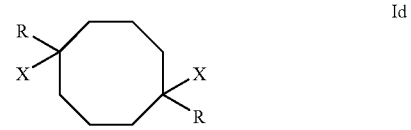
Id

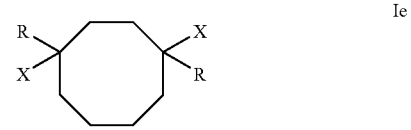
Ie

The novel substituted cycloalkanes of the formula I can be obtained in various ways, for example by addition of a compound HX onto cycloalkadienes or cycloalkatrienes which bear at least one $C_1$-$C_6$-alkyl substituent on the double bonds. The primary addition products can, if desired, be converted into further derivatives.

The present invention therefore also provides a process for preparing a substituted cycloalkane of the formula I, which comprises reacting a cycloalkapolyene of the formula II

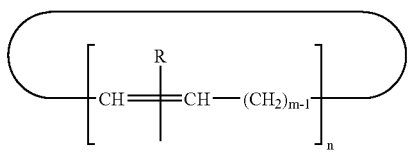
(II)

with a compound HX at below 40° C., where the symbols R, X, m and n are as defined above.

The symbol

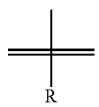

means that one of the two hydrogen atoms on the C=C double bond has been replaced by "R".

It is preferred that all double bonds in the cycloalkapolyenes of the formula II have a cis configuration. The double bonds are preferably not cumulated and preferably not conjugated.

Preferred cycloalkapolyenes have the formulae IIa to IIc below, where
o=1 and p=2, or
o=1 or 2, p=2 or 3 and o+p=4, or
o=1 or 2, p=3 or 4 and o+p=5.

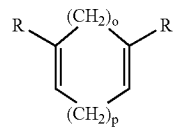
IIa

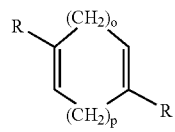
IIb

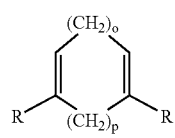
IIc

Particularly preferred cycloalkapolyenes of the formula II are 1,5-dialkylcycloocta-1,5-dienes and 1,6-dialkylcycloocta-1,5-dienes of the formulae IId and IIe:

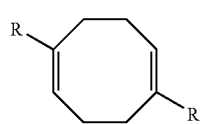
IId

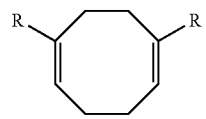
IIe 1,5-Dimethylcycloocta-1,5-diene and 1,6-dimethylcycloocta-1,5-diene are most preferred.

It is also possible to use mixtures of cycloalkapolyenes of the formula II, preferably cycloalkapolyenes having the same ring size and the same number of double bonds. The compounds in the mixture particularly preferably differ only in the position of the substituents R on the double bonds. In particular, 1,5-dimethylcycloocta-1,5-diene or 1,6-dimethylcycloocta-1,5-diene or mixtures thereof are used.

Cycloalkapolyenes of the formula II and methods of preparing them are known. An example which may be mentioned is the preparation of 1,5-dimethylcycloocta-1,5-diene or 1,6-dimethylcycloocta-1,5-diene by dimerization of isoprene (cf. G. A. Tolstikov et al., J. Gen. Chem. USSR (Engl. Transl.); 46, 1976, pp. 188-192; G. S. Hammond et al., J. Org. Chem., 28, 1963, pp. 3297-3303).

The compound HX is advantageously a hydrogen halide or an organic carboxylic acid $R^1COOH$. Examples of suitable hydrogen halides are hydrogen chloride, hydrogen bromide and hydrogen iodide. Examples of suitable organic carboxylic acids $R^1COOH$ are formic acid, acetic acid, propionic acid, butyric acid, isobutyric acid, valeric acid, isovaleric acid and caproic acid.

Preference is given to using a hydrogen halide, in particular hydrogen chloride, as compound HX. The hydrogen halide is preferably used in gaseous form or in the form of a solution in an organic solvent, e.g. a solution of hydrogen chloride or hydrogen bromide in an aliphatic or cyclic ether such as diethyl ether, methyl tert-butyl ether, propyl ether, isopropyl ether, tetrahydrofuran and dioxane. However, the use of gaseous hydrogen halides, in particular gaseous hydrogen chloride, is particularly preferred.

The compound HX is used in at least the stoichiometric amount, based on the double bonds present in the cycloalkapolyene, preferably in a 1.1-fold to 10-fold molar excess.

The reaction is generally carried out at from –25 to +25° C., preferably from –5 to +10° C. The reaction can be carried out either at atmospheric pressure or under superatmospheric pressure. The pressure is preferably from 1 to 10 bar.

The reaction can be carried out in the presence of a solvent. All solvents or solvent mixtures which have a suitable dielectric constant and no abstractable protons and are liquid under the reaction conditions are possible. Examples are aliphatic hydrocarbons, e.g. alkanes having from 4 to 8, preferably from 5 to 8, carbon atoms, e.g. butane, pentane, hexane, heptane, octane and their isomers, haloalkanes such as methyl chloride, methyl bromide, methylene chloride, methylene bromide, trichloromethane, carbon tetrachloride, chloroethane, dichloroethane and trichloroethane, cycloalkanes having from 5 to 8 carbon atoms, e.g. cyclopentane, cyclohexane and cyclooctane, also aromatic hydrocarbons such as benzene, toluene, the xylenes, ethylbenzene, nitrobenzene, chlorobenzene and dichlorobenzene.

However, the reaction is preferably carried out in the absence of a solvent.

If desired, the reaction of the cycloalkapolyene of the formula II with the compound HX can also be carried out in the presence of a catalyst, e.g. a Lewis and/or Brönsted acid.

Suitable Lewis acids include aluminum chloride, boron trifluoride, boron trifluoride alcoholate or etherate, boron trichloride, titanium tetrachloride and tin tetrachloride.

Suitable Brönsted acids are ones which have a greater acid strength than the compound HX. The Brönsted acid can be either an inorganic acid such as sulfuric acid, phosphoric acid or hydrogen iodide, or a strong organic acid such as trifluoroacetic acid or trifluoromethanesulfonic acid. The organic acid can also be present in bound form, e.g. as an ion-exchange resin.

The reaction of the cycloalkapolyene of the formula II and the compound HX can be carried out by customary methods. Thus, for example, it is possible to place the cycloalkapolyene in a reaction vessel at the reaction temperature, if desired in a solvent and if desired together with a catalyst, and add the compound HX. The way in which the compound HX is added depends on the nature of this compound. Thus, hydrogen halides used in gaseous form can be passed through the initially charged starting material or through its solution. As an alternative, the reaction can be carried out in a pressure vessel into which the full amount of the hydrogen halide to be used is introduced, and the reaction mixture is then left or mixed for the required reaction time. As an alternative, the hydrogen halide can also be introduced into the pressure vessel gradually, if desired in an amount corresponding to the amount which has been consumed. When hydrogen halide solutions are used, these can be added all at once or preferably a little at a time or continuously to the cycloalkapolyene of the formula II or its solution. Organic carboxylic acids HX can be used in neat form or in solution.

The work-up is carried out by conventional methods. Thus, excess hydrogen halide can be removed, for example by stripping with an inert gas such as nitrogen or by distillation, e.g. under reduced pressure. If the reaction has been carried out in the absence of a solvent and without a catalyst, further purification of the product is frequently superfluous. When the reaction has been carried out in solution, the solvent is generally removed after removal of the hydrogen halide, for example by distillation. When acids $R^1COOH$ are used as compounds HX or the reaction is carried out in the presence of Lewis or Brönsted acids, these are usually removed by extraction, e.g. by extraction of the reaction mixture with water or an aqueous base.

The product can subsequently be purified by conventional methods, for example by distillation, in particular under reduced pressure. However, the process of the present invention frequently gives the reaction product in a purity which is sufficient for further applications without purification.

Compounds I, in which X is a radical $OR^1$ can also be obtained by reacting a substituted cycloalkane of the formula I, in which X is halogen with an alcohol $R^1OH$ under conditions known to those skilled in the art for nucleophilic substitution.

The invention further provides a process for cationic polymerization which comprises polymerizing cationically polymerizable ethylenically unsaturated monomers in the presence of a substituted cycloalkane of the formula I and a Lewis acid. Depending on the substituted cycloalkane of the formula I, linear polymers (when n=2) or star-shaped polymers (when n=3) are obtained.

Possible cationically polymerizable ethylenically unsaturated monomers are, in particular, isobutene, vinylaromatic compounds such as styrene and α-methylstyrene or isoolefins having from 5 to 10 carbon atoms, e.g. 2-methyl-1-butene, 2-methyl-1-pentene, 2-methyl-1-hexene, 2-ethyl-1-pentene, 2-ethyl-1-hexene and 2-propyl-1-heptene. The process is preferably employed for preparing homopolymers, copolymers or block copolymers of isobutene.

As Lewis acid, it is possible to use covalent metal halides and semimetal halides which have an electron pair gap. Such compounds are known to those skilled in the art, for example from J. P. Kennedy et al. in U.S. Pat. No. 4,946,889, U.S. Pat. No. 4,327,201, U.S. Pat. No. 5,169,914, EP-A-206 756, EP-A-265 053 and also, in summary, in J. P. Kennedy, B. Ivan, "Designed Polymers by Carbocationic Macromolecular Engineering", Oxford University Press, New York, 1991. Lewis acids which are particularly preferred for the polymerization of isobutene are titanium tetrachloride, boron trichloride and boron trifluoride, in particular titanium tetrachloride.

It has been found to be useful to carry out the polymerization in the presence of an electron donor. Possible electron donors are aprotic organic compounds which have a free electron pair located on a nitrogen, oxygen or sulfur atom. Preferred donor compounds are selected from among pyridines such as pyridine itself, 2,6-dimethylpyridine and also sterically hindered pyridines such as 2,6-diisopropylpyridine and 2,6-di-tert-butylpyridine; amides, in particular N,N-dialkylamides of aliphatic or aromatic carboxylic acids, e.g. N,N-dimethylacetamide; lactams, in particular N-alkyllactams such as N-methylpyrrolidone; ethers, e.g. dialkyl ethers such as diethyl ether and diisopropyl ether, cyclic ethers such as tetrahydrofuran; amines, in particular trialkylamines such as triethylamine; esters, in particular $C_1$-$C_4$-alkyl esters of aliphatic $C_1$-$C_6$-carboxylic acids, e.g. ethyl acetate; thioethers, in particular dialkylthioethers or alkyl aryl thioethers, e.g. methyl phenyl sulfide; sulfoxides, in particular dialkyl sulfoxides such as di-methyl sulfoxide; nitriles, in particular alkyl nitriles such as acetonitrile and propionitrile; phosphines, in particular trialkylphosphines or triarylphosphines, e.g. trimethylphosphine, triethylphosphine, tri-n-butylphosphine and triphenylphosphine, and non-polymerizable, aprotic organosilicon compounds bearing at least one organic radical bound via oxygen.

Among the abovementioned donors, preference is given to pyridine and sterically hindered pyridine derivatives and also, in particular, organosilicon compounds. Examples of such preferred compounds are dimethoxydiisopropylsilane, dimethoxyisobutylisopropylsilane, dimethoxydiisobutylsilane, dimethoxydicyclopentasilane, dimethoxyisobutyl-2-butylsilane, diethoxyisobutylisopropylsilane, triethoxytolylsilane, triethoxybenzylsilane and triethoxyphenylsilane.

The Lewis acid is used in an amount sufficient to form the initiator complex. The molar ratio of Lewis acid to initiator is generally from 10 n:1 to 1 n:1, in particular from 2.5 n:1 to 1 n:1, where n is the functionality of the initiator.

Suitable isobutene feedstocks are isobutene itself and also isobutene-containing $C_4$-hydrocarbon streams, for example $C_4$ raffinates, $C_4$ fractions from the dehydrogenation of isobutane, $C_4$ fractions from steam crackers, FCC plants (FCC: fluid catalytic cracking), as long as they have largely been freed of 1,3-butadiene present therein. $C_4$-hydrocarbon streams which are suitable for the purposes of the present invention generally contain less than 500 ppm, preferably less than 200 ppm, of butadiene. When $C_4$ fractions are used as starting material, the hydrocarbons other than isobutene take on the role of an inert solvent.

It is also possible to use monomer mixtures of isobutene with olefinically unsaturated monomers which can be copolymerized with isobutene under cationic polymerization conditions. The process of the present invention is also suitable for the block copolymerization of isobutene with ethylenically unsaturated comonomers which can be polymerized under cationic polymerization conditions. If monomer mixtures of isobutene with suitable comonomers are polymerized, the monomer mixture preferably comprises more than 80% by weight, in particular more than 90% by weight and particularly preferably more than 95% by weight, of isobutene and less than 20% by weight, more preferably less than 10% by weight and in particular less than 5% by weight, of comonomers.

Possible copolymerizable monomers are vinylaromatics such as styrene and $C_1$-$C_4$-alkylstyrenes such as 2-, 3- and 4-methylstyrene, and also 4-tert-butylstyrene, n-butene, isoolefins having from 5 to 10 carbon atoms, e.g. 2-methyl-1-butene, 2-methyl-1-pentene, 2-methyl-1-hexene, 2-ethyl-1-pentene, 2-ethyl-1-hexene and 2-propyl-1-heptene. Further suitable comonomers are olefins which bear a silyl group, e.g. 1-trimethoxysilylethene, 1-(trimethoxysilyl)propene, 1-(trimethoxysilyl)-2-methyl-2-propene, 1-[tri(methoxyethoxy)silyl]ethene, 1-[tri(methoxyethoxy)silyl]propene, and 1-[tri(methoxyethoxy)silyl]-2-methyl-2-propene.

The polymerization is usually carried out in a solvent. Possible solvents are all low molecular weight, organic compounds or mixtures thereof which have a suitable dielectric constant and no abstractable proteins and are liquid under the polymerization conditions. Preferred solvents are hydrocarbons, e.g. acyclic hydrocarbons having from 2 to 8 and preferably from 3 to 8 carbon atoms, e.g. ethane, isopropane and n-propane, n-butane and its isomers, n-pentane and its isomers, n-hexane and its isomers, and also n-heptane and its isomers, and n-octane and its isomers, cyclic alkanes having from 5 to 8 carbon atoms, e.g. cyclopentane, methylcyclopentane, cyclohexane, methylcyclohexane, cycloheptane, acyclic alkenes having preferably from 2 to 8 carbon atoms, e.g. ethene, isopropene and n-propene, n-butene, n-pentene, n-hexene and n-heptene, cyclic olefins such as cyclopentene, cyclohexene and cycloheptene, aromatic hydrocarbons such as toluene, xylene, ethylbenzene, and also halogenated hydrocarbons such as halogenated aliphatic hydrocarbons, e.g. chloromethane, dichloromethane, trichloromethane, chloroethane, 1,2-dichloroethane and 1,1,1-trichloroethane and 1-chlorobutane, and also halogenated aromatic hydrocarbons such as chlorobenzene and fluorobenzene. The halogenated hydrocarbons used as solvents do not include compounds in which halogen atoms are located on secondary or tertiary carbon atoms.

Particularly preferred solvents are aromatic hydrocarbons, among which toluene is particularly preferred. Preference is likewise given to solvent mixtures comprising at least one halogenated hydrocarbon and at least one aliphatic or aromatic hydrocarbon. In particular, the solvent mixture comprises hexane and chloromethane and/or dichloromethane. The volume ratio of hydrocarbon to halogenated hydrocarbon is preferably in the range from 1:10 to 10:1, particularly preferably in the range from 4:1 to 1:4 and in particular in the range from 2:1 to 1:2.

In general, the cationic polymerization is carried out at below 0° C., e.g. in the range from 0 to −140° C., preferably in the range from −30 to −120° C., and particularly preferably in the range from −40 to −110° C. The reaction pressure is of subordinate importance.

The heat of reaction is removed in a conventional fashion, for example by wall cooling and/or by means of evaporative cooling. Here, the use of ethene and/or mixtures of ethene with the solvents mentioned above as preferred has been found to be particularly useful.

To prepare block copolymers, the distal end of the chain, i.e. the end of the isobutene polymer which is farthest from the initiator, can be reacted with comonomers such as those mentioned above, e.g. vinylaromatics. Thus, for example, isobutene can be homopolymerized first and the comonomer can be added subsequently. The newly formed reactive chain end derived from the comonomer is either deactivated or, according to one of the embodiments described below, terminated to form a functional end group or reacted further with isobutene to form higher block copolymers.

To stop the reaction, the living chain ends are deactivated, for example by addition of a protic compound, in particular by addition of water, alcohols such as methanol, ethanol, n-propanol, isopropanol, n-butanol, isobutanol, sec-butanol or tert-butanol, or mixtures of these with water.

To obtain bifunctional or trifunctional (telechelic) isobutene polymers, the distal end of the chain is terminated to form an ethylenically unsaturated group, with the reactive chain end being, for example, reacted with a terminating reagent which attaches an ethylenically unsaturated group to the end of the chain, or appropriately treated to convert the reactive chain end into such a group.

In one embodiment, the chain end is terminated by addition of a trialkylallylsilane compound, e.g. trimethylallylsilane. The use of allylsilanes leads to termination of the polymerization with introduction of an allyl radical at the end of the polymer chain, cf. EP 264 214.

In a further embodiment, the reactive chain end is converted thermally, for example by heating to from 70 to 200° C., or by treatment with a base, into a methylidene double bond. Suitable bases are, for example, alkali metal alkoxides such as sodium methoxide, sodium ethoxide and potassium tert-butoxide, basic aluminum oxide, alkali metal hydroxides such as sodium hydroxide and tertiary amines such as pyridine or tributylamine, cf. Kennedy et al., Polymer Bulletin 1985, 13, 435-439. Preference is given to using sodium ethoxide.

In a further embodiment, the reactive chain end is reacted with a conjugated diene such as butadiene, cf. DE-A 40 25 961.

In a further embodiment, two or more living polymer chains are coupled by addition of a coupling agent. "Coupling" in this context means the formation of chemical bonds between the reactive chain ends, so that two or more polymer chains are joined to form a single molecule.

Suitable coupling agents have, for example, at least two electrofugic leaving groups, e.g. trialkylsilyl groups, located in allylic positions relative to the same or different double bonds, so that the cationic center of a reactive chain end can add on in a concerted reaction with elimination of the leaving group and shifting of the double bond. Other coupling agents have at least one conjugated system onto which the cationic center of a reactive chain end can add electrophilically to form a stabilized cation. Elimination of a leaving group, e.g. a proton, then results in formation of a stable s bond to the polymer chain with reformation of the conjugated system. A plurality of these conjugated systems can be joined to one another via inert spacers.

Suitable coupling agents include:

(i) compounds which have at least two 5-membered heterocycles containing a heteroatom selected from among oxygen, sulfur and nitrogen, for example organic compounds containing at least two furan rings, e.g.

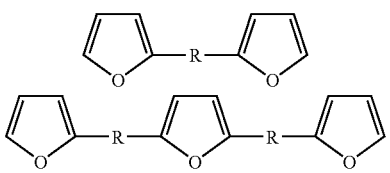

where R is $C_1$-$C_{10}$-alkylene, preferably methylene of 2,2-propanediyl;

(ii) compounds having at least two trialkylsilyl groups in allylic positions, for example 1,1-bis(trialkylsilylmethyl)ethylenes, e.g. 1,1-bis(trimethylsilylmethyl)ethylene, bis[(trialkylsilyl)propenyl]benzenes, e.g.

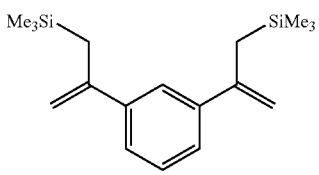

(where Me is methyl);

(iii) compounds having at least two vinylidene groups which are each conjugated with two aromatic rings, for example bisdiphenylethylenes, e.g.

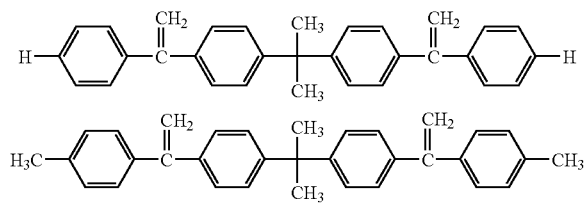

A description of suitable coupling agents may be found in the following literature references; the coupling reaction can be carried out in a manner analogous to the reactions described there: R. Faust, S. Hadjikyriacou, Macromolecules 2000, 33, 730-733; R.

Faust, S. Hadjikyriacou, Macromolecules 1999, 32, 6393-6399; R. Faust, S. Hadjikyriacou, Polym. Bull. 1999, 43, 121-128; R. Faust, Y. Bae, Macromolecules 1997, 30, 198; R. Faust, Y. Bae, Macromolecules 1998, 31, 2480; R. Storey, Maggio, Polymer Preprints 1998, 39, 327-328; WO99/24480; U.S. Pat. No. 5,690,861 and U.S. Pat. No. 5,981,785.

The coupling reaction is generally carried out in the presence of a Lewis acid. Suitable Lewis acids are those which can also be used for carrying out the actual polymerization reaction. In addition, solvents and temperatures suitable for carrying out the coupling reaction are the same as those used for carrying out the actual polymerization reaction. The coupling reaction can therefore advantageously be carried out as a one-pot reaction subsequent to the polymerization reaction in the same solvent in the presence of the Lewis acid used for the polymerization. It is usual to use a molar amount of the coupling agent which corresponds approximately to the molar amount of the initiator of the formula I used for the polymerization divided by the number of coupling sites of the coupling agent.

After the termination or coupling reaction, the solvent is generally removed in suitable apparatuses such as rotary evaporators, falling film evaporators or thin film evaporators or by depressurization of the reaction solution.

The isobutene polymers prepared by the process of the present invention have a narrow molecular weight distribution. The polydispersity index $PDI=M_w/M_n$ is preferably below 1.40, particularly preferably below 1.35.

The telechelic polyisobutenes can be subjected to one of the following derivative-formation reactions:

Electrophilic Substitution on Aromatics

The polyisobutene can be reacted with a (hetero)aromatic compound in the presence of an alkylation catalyst. Suitable aromatic and heteroaromatic compounds, catalysts and reaction conditions for this Friedel-Crafts alkylation are described, for example, in J. March, Advanced Organic Chemistry, $4^{th}$ edition, John Wiley & Sons, pp. 534-539, which is hereby incorporated by reference.

Phenolic compounds which have 1, 2 or 3 OH groups and may have at least one further substituent are particularly useful. Preferred further substituents are methyl and ethyl. Particular preference is given to phenol, the cresol isomers, catechol, resorcinol, pyrogallol, fluoroglucinol and the xylenol isomers. Very particular preference is given to using phenol, o-cresol and p-cresol.

Examples of suitable catalysts are $AlCl_3$, $AlBr_3$, $BF_3$, $BF_3 \cdot 2\ C_6H_5OH$, $BF_3[O(C_2H_5)_2]_2$, $TiCl_4$, $SnCl_4$, $AlC_2H_5Cl_2$, $FeCl_3$, $SbCl_5$ and $SbF_5$. These alkylation catalysts can be used together with a cocatalyst, for example an ether, such as dimethyl ether, diethyl ether, di-n-propyl ether or tetrahydrofuran. The reaction can also be catalyzed by protic acids such as sulfuric acid, phosphoric acid or trifluoromethanesulfonic acid. Organic protic acids can also be present in polymer-bound form, for example as ion-exchange resin. Zeolites and inorganic polyacids are also useful.

The alkylation can be carried out in the presence or absence of a solvent. Suitable solvents are, for example, n-alkanes and mixtures thereof and alkylaromatics such as toluene, ethylbenzene and xylene and also halogenated derivatives thereof.

To carry out further functionalization, the polyisobutenylphenol obtained can be subjected to a Mannich reaction with at least one aldehyde, preferably formaldehyde, and at least one amine which has at least one primary or secondary amine function, resulting in a compound which is alkylated with polyisobutene and is additionally at least partially aminoalkylated. It is also possible to use reaction and/or condensation products of aldehyde and/or amine. The preparation of such compounds is described in WO 1/25 293 and WO 01/25 294, which are hereby fully incorporated by reference.

Epoxidation

The polyisobutene can be epoxidized by means of a peroxide compound. Suitable methods of carrying out the epoxidation are described in J. March, Advanced Organic Chemistry, $4^{th}$ edition, John Wiley & Sons, pp. 826-829, which is hereby incorporated by reference. As peroxide compound, preference is given to using at least one peracid such as m-chloroperbenzoic acid, performic acid, peracetic acid, trifluoroperacetic acid, perbenzoic acid and 3,5-dinitroperbenzoic acid. The peracids can be prepared in situ from the corresponding acids and $H_2O_2$, if appropriate in the presence of mineral acids.

Further suitable epoxidation reagents are, for example, alkali hydrogen peroxide, molecular oxygen and alkyl peroxides such as tert-butyl hydroperoxide. Suitable solvents for the epoxidation are, for example, customary nonpolar solvents. Particularly useful solvents are hydrocarbons such as toluene, xylene, hexane or heptane. The epoxide formed can subsequently be reacted with water, acids, alcohols, thiols or primary or secondary amines to open the ring and form, inter alia, diols, glycol ethers, glycol thioethers and amines.

Hydroboration

The polyisobutene can be reacted with a borane (if desired a borane generated in situ) to give an at least partially hydroxylated polyisobutene. Suitable methods of carrying out the hydroboration are described in J. March, Advanced Organic Chemistry, 4$^{th}$ edition, Verlag John Wiley & Sons, pp. 783-789, which is hereby incorporated by reference. Suitable hydroboration reagents are, for example, diborane which is usually generated in situ by reaction of sodium borohydride with $BF_3$etherate, diisoamylborane (bis[3-methylbut-2-yl]borane), 1,1,2-trimethylpropylborane, 9-borabicyclo[3.3.1]nonane, diisocamphenylborane, which can be obtained by hydroboration of the corresponding alkenes by diborane, chloroborane dimethyl sulfide, alkyldichloroboranes or $H_3B—N(C_2H_5)_2$.

The alkylboranes formed are usually not isolated but converted by subsequent reaction directly into the desired products. A very important reaction of alkylboranes is the reaction with alkaline hydrogen peroxide to give an alcohol which preferably corresponds formally to the anti-Markovnikov hydration of the alkene. Furthermore, the alkylboranes obtained can be subjected to reaction with bromine in the presence of hydroxide ions to give the bromide.

Ene Reaction

The polyisobutene can be reacted with at least one alkene having an electrophilically substituted double bond in an ene reaction (cf., for example, DE-A 4 319 672 or H. Mach and P. Rath in "Lubrication Science 11 (1999), pp. 175-185, which are hereby fully incorporated by reference). In the ene reaction, the alkene having an allylic hydrogen atom, referred to as ene, is reacted with an electrophilic alkene, viz. the enophile, in a pericyclic reaction encompassing a carbon-carbon bond formation, a double bond shift and a hydrogen transfer. In the present case, the polyisobutene reacts as the ene. Suitable enophiles are compounds as are also used as dienophiles in the Diels-Alder reaction. Preference is given to using maleic anhydride as enophile. This results in polyisobutenes functionalized at least partly with succinic anhydride groups.

The polyisobutene modified with succinic anhydride groups can be subjected to a further reaction selected from among:

α) reaction with at least one amine to give a polyisobutene functionalized at least partly with succinimide groups and/or succinamide groups, β) reaction with at least one alcohol to give a polyisobutene functionalized at least partly with succinic ester groups, and γ) reaction with at least one thiol to give a polyisobutene functionalized at least partly with succinic thioester groups.

The following examples illustrate the invention.

EXAMPLES

Example 1

Reaction of 1,5-dimethylcycloocta-1,5-diene with Hydrogen Chloride Gas in Methylene Chloride 100 g (0.73 mol) of 1,5-dimethylcycloocta-1,5-diene together with 200 ml of methylene chloride were placed in a 500 ml four-necked flask. While cooling to an internal temperature of 0-5° C., 60 g (1.64 mol) of hydrogen chloride were fed in at atmospheric pressure over a period of 4 hours. Unreacted hydrogen chloride was subsequently removed by stripping with nitrogen. The solvent was then removed completely under reduced pressure. The product was finally purified by distillation (boiling point: 85-88° C. at 2 mbar) to give 137.1 g (90% of theory) of 1,5-dichloro-1,5-dimethylcyclooctane as a colorless liquid. $^1$H-NMR (CDCl$_3$; 500 MHz): 2.40-2.25 (m); 2.20-1.95 (m); 1.8-1.7 (m); 1.7-1.5 (m). $^{13}$C{$^1$H}-NMR (CDCl$_3$; 400 MHz): 74.6 (s, 2C); 42.4 (s, 4C); 34.5 (s, 2C); 21.5 (s, 2C).

Example 2

Reaction of 1,5-dimethylcycloocta-1,5-diene with Hydrogen Chloride Gas 250 g (1.83 mol) of 1,5-dimethylcycloocta-1,5-diene were placed in a 2 l four-necked flask. While cooling to an internal temperature of 0-10° C., 140 g (3.84 mol) of hydrogen chloride were fed in at atmospheric pressure over a period of 8 hours. Unreacted hydrogen chloride was subsequently removed under reduced pressure and the product was purified by distillation (boiling point: 85-88° C. at 2 mbar) to give 357.6 g (93% of theory) of 1,5-dichloro-1,5-dimethylcyclooctane as a colorless liquid. $^1$H-NMR (CDCl$_3$; 500 MHz): 2.40-2.25 (m); 2.20-1.95 (m); 1.8-1.7 (m); 1.7-1.5 (m). $^{13}$C{$^1$H}-NMR (CDCl$_3$; 400 MHz): 74.5 (s, 2C); 42.3 (s, 4C); 34.5 (s, 2C); 21.6 (s, 2C).

Example 3

Reaction of an Isomer Mixture of 1,5-dimethylcycloocta-1,5-diene (84%) and 1,6-dimethylcycloocta-1,6-diene (16%) with Hydrogen Chloride Gas in Hexane 150 g (1.10 mol) of the isomer mixture together with 200 ml of hexane were placed in a 500 ml four-necked flask. While cooling to an internal temperature of 5-10° C., 79 g (2.16 mol) of hydrogen chloride were fed in at atmospheric pressure over a period of 5.5 hours. Unreacted hydrogen chloride and the solvent were subsequently removed completely under reduced pressure. This gave 191.2 g (91% of theory) of a mixture of 1,5-dichloro-1,5-dimethylcyclooctane (A) and 1,4-dichloro-1,4-dimethylcyclooctane (B) as a colorless liquid. The product was finally purified by distillation (boiling point: 83-88° C. at 2 mbar). $^1$H-NMR (CDCl$_3$; 500 MHz): 2.40-2.25 (m); 2.20-1.95 (m); 1.8-1.7 (m); 1.7-1.5 (m). $^{13}$C{$^1$H}-NMR (CDCl$_3$; 400 MHz): 74.6 (s, 2C, A); 74.5 (s, 2C, B); 42.4 (s, 4C, B); 42.3 (s, 4C, A); 34.7 (s, 2C, B); 34.5 (s, 2C, A); 21.6 (s, 2C, A); 20.9 (s, 2C, B).

Example 4

Reaction of an Isomer Mixture of 1,5-dimethylcycloocta-1,5-diene (84%) and 1,6-dimethylcycloocta-1,6-diene (16%) with Hydrogen Chloride Gas 380 g (2.79 mol) of the isomer mixture were placed in an autoclave. 210 g (5.76 mol) of hydrogen chloride were fed in over a period of 3 hours in such a way that the internal pressure was 5 bar and the internal temperature did not exceed 25° C. Unreacted hydrogen chloride was subsequently removed by stripping with nitrogen. The product was finally purified by distillation (boiling point: 83-88° C. at 2 mbar) to give 568.7 g (97% of theory) of a mixture of 1,5-dichloro-1,5-dimethylcyclooctane (A) and 1,4-dichloro- 1,4-dimethylcyclooctane (B) as a colorless liquid. $^1$H-NMR (CDCl$_3$; 500 MHz): 2.40-2.25 (m); 2.20-1.95 (m); 1.8-1.7 (m); 1.7-1.5 (m). $^{13}$C{$^1$H}-NMR (CDCl$_3$; 400 MHz): 74.5 (s, 2C, A); 74.5 (s, 2C, B); 42.4 (s, 4C, B); 42.3 (s, 4C, A); 34.7 (s, 2C, B); 34.6 (s, 2C, A); 21.6 (s, 2C, A); 21.0 (s, 2C, B).

Example 5

Polymerization of an Isobutene Oligomer Having a Mean Molecular Weight of 5000 g/mol 300 ml of n-hexane which had been dried overnight over molecular sieves (3 Å) were placed in a 2 l glass flask which had been rendered inert by means of dry nitrogen. 300 ml of dichloromethane were subsequently added via a dropping funnel filled with aluminum oxide spheres. The solution was admixed with a spatula tip of phenanthroline and cooled to −40° C. At this temperature, the residual water present was titrated with n-butyllithium until a brown coloration was obtained. The mixture was then heated and the dried solvents were transferred via a Teflon tube provided with a Jäger valve into the actual reaction flask which had previously been rendered inert by means of dry nitrogen. The solvents were again cooled (−70° C.). 400 ml of isobutene were passed in gaseous form over molecular sieves (3 Å), dried in this way and condensed into a dropping funnel which was cooled by means of dry ice/acetone and had been plugged into the top of the reaction flask, and the isobutene was subsequently drained into the reaction flask. At −70° C., 1.475 g of phenyltriethoxysilane and 10.46 g of initiator were then introduced into the reaction flask while stirring. Shortly afterwards, 4.93 g of TiCl$_4$ were introduced to start the reaction. A temperature increase to −50° C. was observed. The reaction was continued at −50° C. for 2 hours and then stopped by means of ethanol. The reaction flask was then warmed to room temperature and the contents were washed with one liter of deionized water in a shaking funnel. After phase separation, the aqueous phase was discarded and the organic phase was washed once more with one liter of water. After the aqueous phase had been separated off again, the organic phase was filtered with suction through silica gel and evaporated to dryness at 180° C. and 3 mbar. A colorless, highly viscous polymer remained.

Analysis: GPC: gel permeation chromatography was carried out using a combination of two Styragel columns (1000 and 10000 Å). Calibration was carried out using isobutene standards. $M_n$: 5700 g/mol, $M_w$: 10249 g/mol; D: 1.7; m.p.: 63635 g/mol.

We claim:

1. A substituted cycloalkane of the formulae Ia, Ib, and Ic:

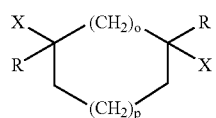

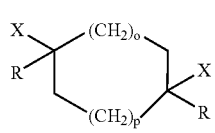

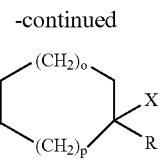

wherein

R is C$_1$-C$_6$-alkyl;

X is halogen, OR$^1$ or OCOR$^1$, wherein R$^1$ is C$_1$-C$_6$-alkyl; and o=1 and p=2, or o=1 or 2, p=2 or 3 and o+p=4, or o=1 or 2, p=3 or 4 and o+p=5.

2. The compound as claimed in claim 1, wherein R is methyl.

3. The compound as claimed in claim 1, wherein X is chlorine.

4. The compound as claimed in claim 1, selected from the group consisting of 1,4-dichloro-1,4-dimethylcyclooctane, 1,5-dichloro-1,5-dimethylcyclooctane and mixtures thereof.

5. A process for preparing a substituted cycloalkane of the formulae Ia, Ib, and Ic as claimed in claim 1, which comprises reacting a cycloalkapolyene of the formulae IIa, IIb, and IIc

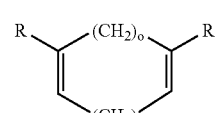

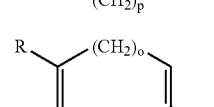

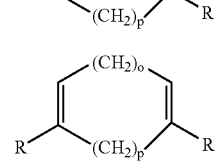

with a compound HX at below 40° C., where the symbols R, X, o and p are as defined in claim 1.

6. The process as claimed in claim 5, wherein the compound HX used is gaseous hydrogen chloride.

7. The process as claimed in claim 5, wherein the cycloalkapolyene of the formula II used is 1,5-dimethylcycloocta-1,5-diene and/or 1,6-dimethylcycloocta-1,5-diene.

8. The process as claimed in claim 5, wherein the reaction is carried out in the absence of a solvent or in the presence of an aprotic solvent.

9. A cationic polymerization process which comprises polymerizing cationically polymerizable ethylenically unsaturated monomers in the presence of a substituted cycloalkane of the formula I as claimed in claim 1 and a Lewis acid.

10. The process as claimed in claim 9, wherein the compound of the formula I is 1,5-dichloro-1,5-dimethylcyclooctane and/or 1,4-dichloro-1,4-dimethylcyclooctane.

11. The process as claimed in claim 9, wherein the cationically polymerizable ethylenically unsaturated monomers include isobutene.

* * * * *